United States Patent [19]

Foshee et al.

[11] Patent Number: 5,282,800
[45] Date of Patent: Feb. 1, 1994

[54] SURGICAL INSTRUMENT

[75] Inventors: David L. Foshee; Warren Taylor, both of Cary, N.C.

[73] Assignee: Edward Weck, Inc., Research Triangle Park, N.C.

[21] Appl. No.: 947,776

[22] Filed: Sep. 18, 1992

[51] Int. Cl.⁵ .............................................. A61B 17/39
[52] U.S. Cl. .............................. 606/52; 606/41; 606/205; 606/208
[58] Field of Search ............... 606/41, 45–52, 606/170, 205–211, 142, 143; 128/4–6, 749, 751, 754

[56] References Cited

U.S. PATENT DOCUMENTS

| | | | |
|---|---|---|---|
| 1,813,902 | 1/1928 | Bovie | 606/52 |
| 2,004,559 | 6/1935 | Wappler et al. | 606/46 |
| 2,090,923 | 8/1937 | Wappler | 606/46 |
| 2,113,246 | 5/1937 | Wappler | 606/46 |
| 2,790,437 | 4/1957 | Moore | 128/751 |
| 3,939,840 | 2/1976 | Storz | 606/46 |
| 4,005,714 | 2/1977 | Hiltebrandt | 606/51 |
| 4,134,406 | 1/1979 | Iglesias | 606/46 |
| 4,258,716 | 3/1981 | Sutherland | 606/170 |
| 4,569,131 | 2/1986 | Falk et al. | 128/751 |
| 4,574,803 | 3/1986 | Storz | 606/171 |
| 4,635,634 | 1/1987 | Santos | 606/142 |
| 4,649,917 | 3/1987 | Karasawa | 606/46 |
| 4,657,016 | 4/1987 | Garito et al. | 606/45 |
| 4,732,149 | 3/1988 | Sutter | 606/51 |
| 4,971,067 | 11/1990 | Bolduc et al. | 128/751 |
| 5,084,057 | 1/1992 | Green et al. | 606/142 |

*Primary Examiner*—Stephen C. Pellegrino
*Assistant Examiner*—Mike Peffley
*Attorney, Agent, or Firm*—Arnold, White & Durkee

[57] ABSTRACT

A surgical instrument consisting of a disposable working member and a reusable handle member. The surgical instrument reduces the risk of cross-contamination as the parts of the instrument which enter the body cavity are disposable. The reusable handle is designed for quick and easy loading and unloading of the disposable working member or stem assembly. The reusable handle may be used with stem assemblies of various types, sizes and shapes.

10 Claims, 10 Drawing Sheets

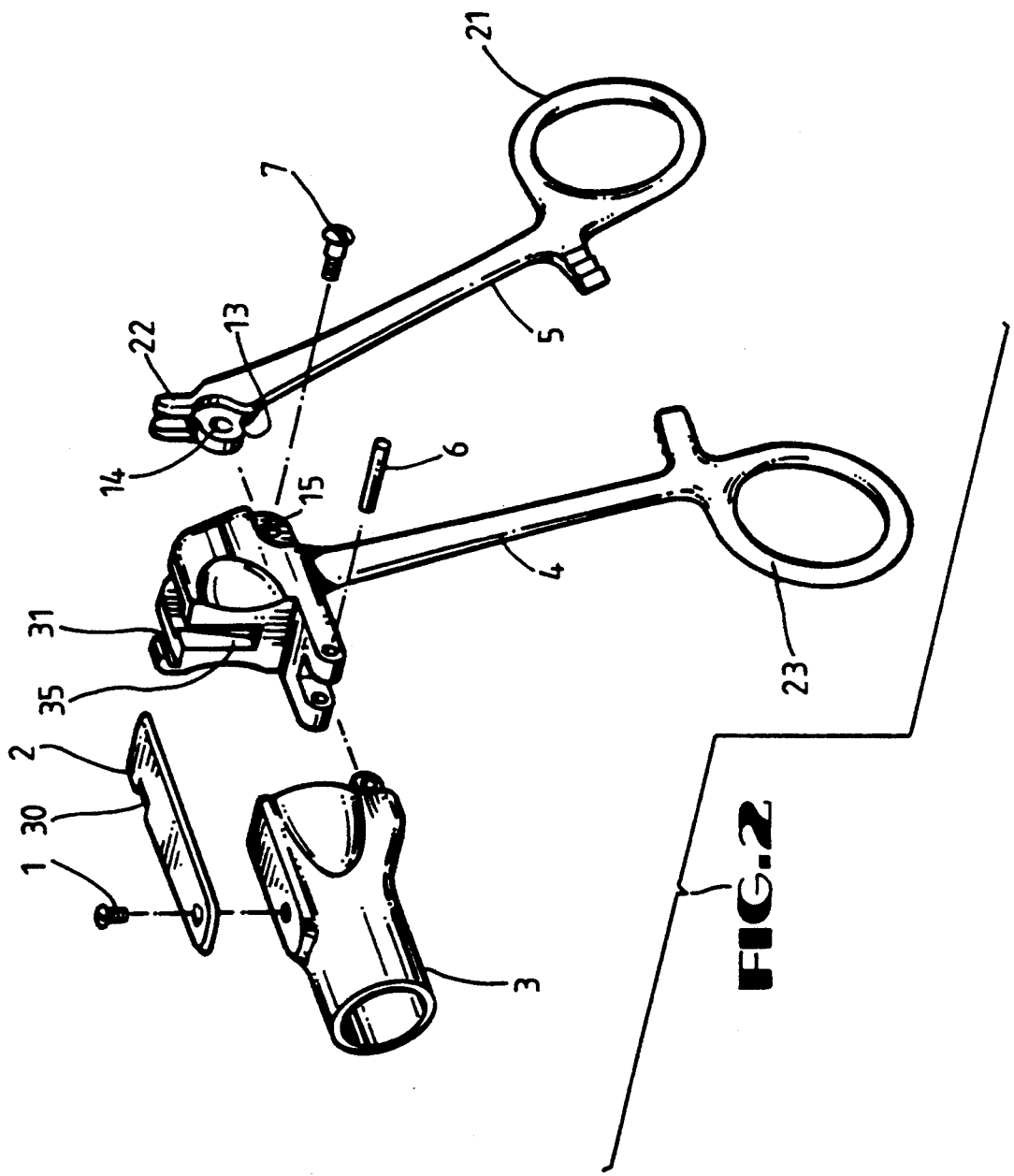

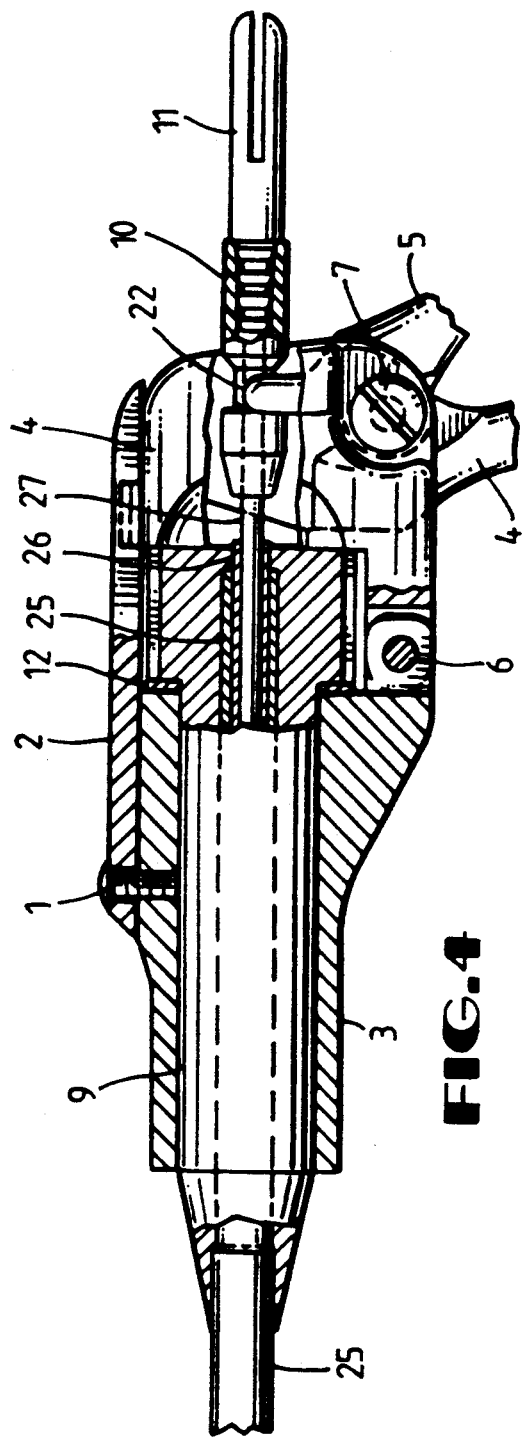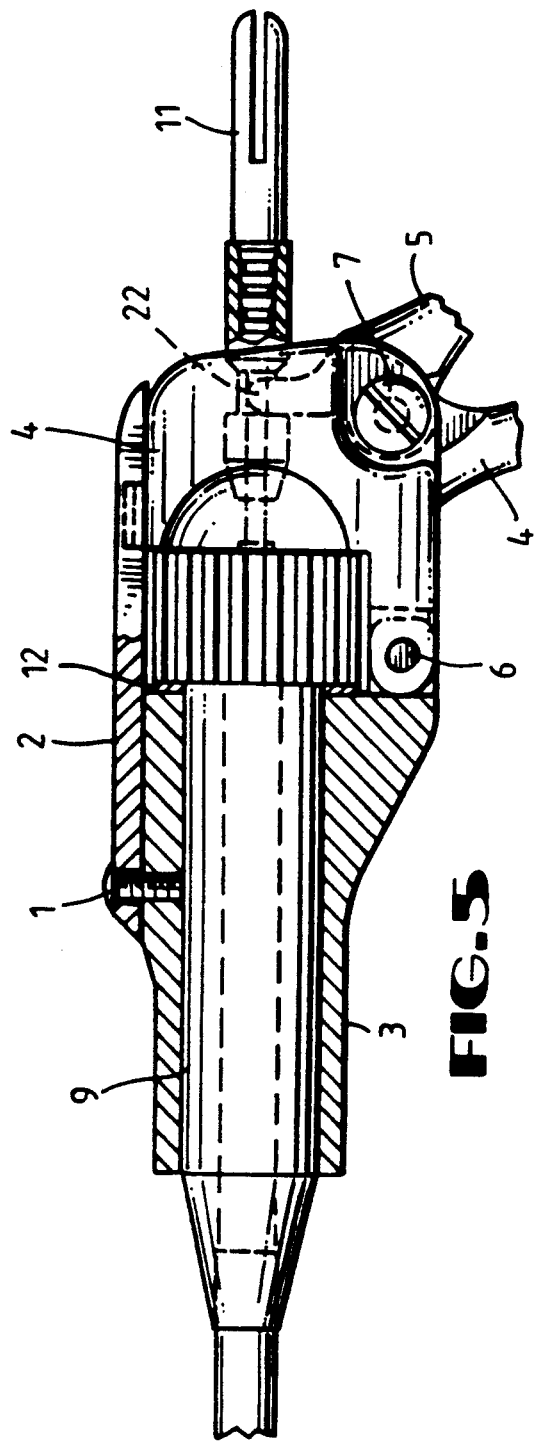

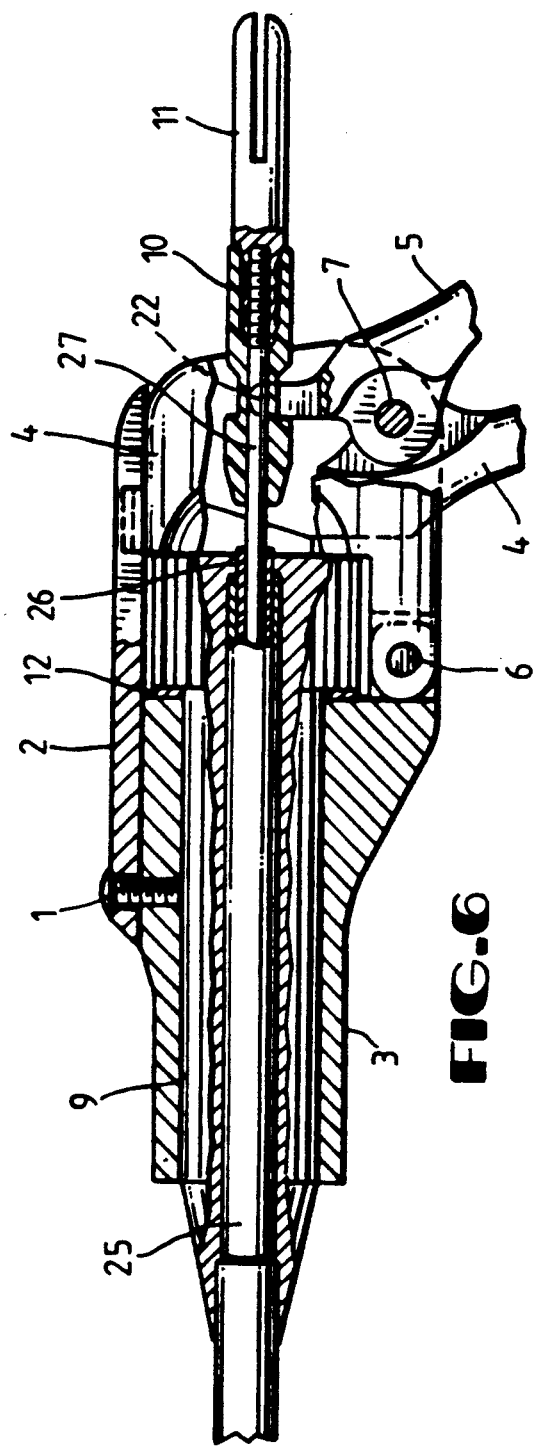
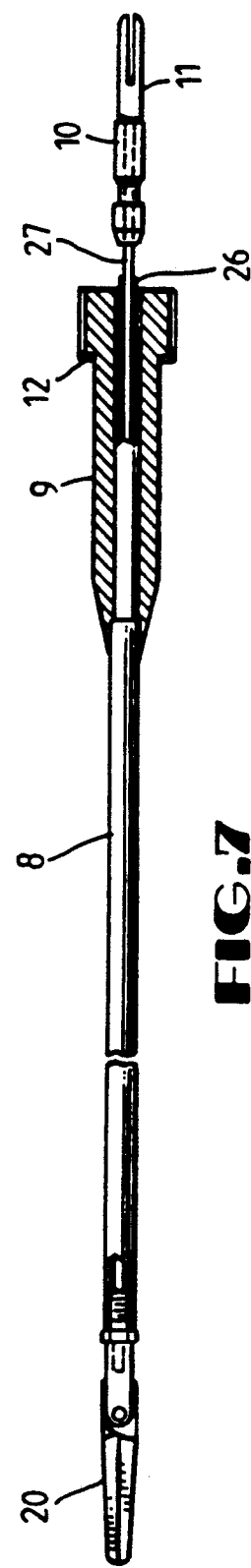
FIG.6
FIG.7

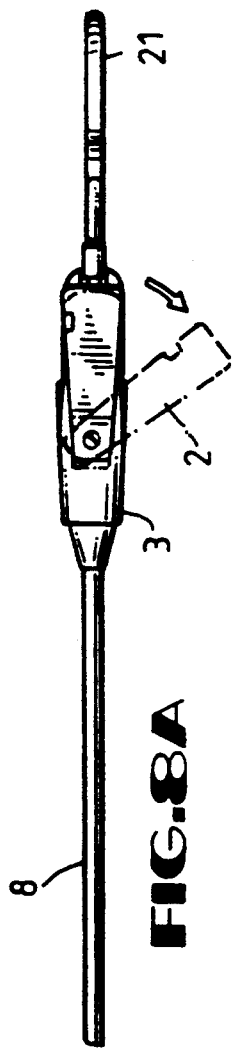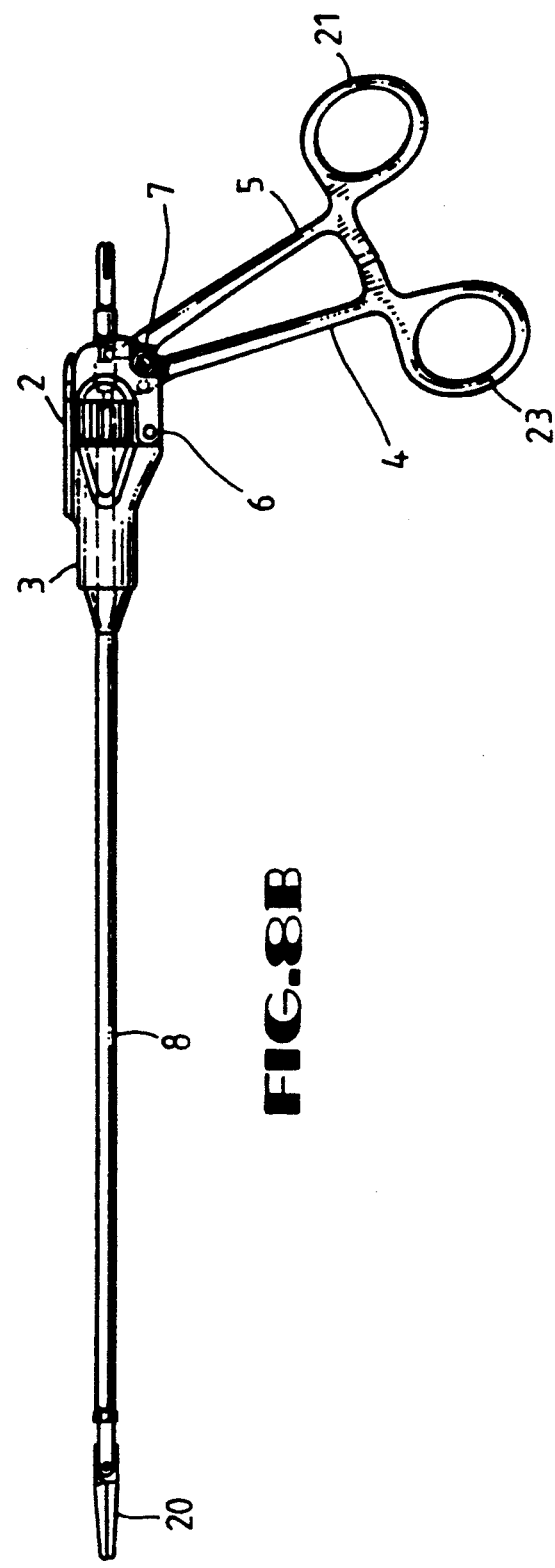
FIG.8A
FIG.8B

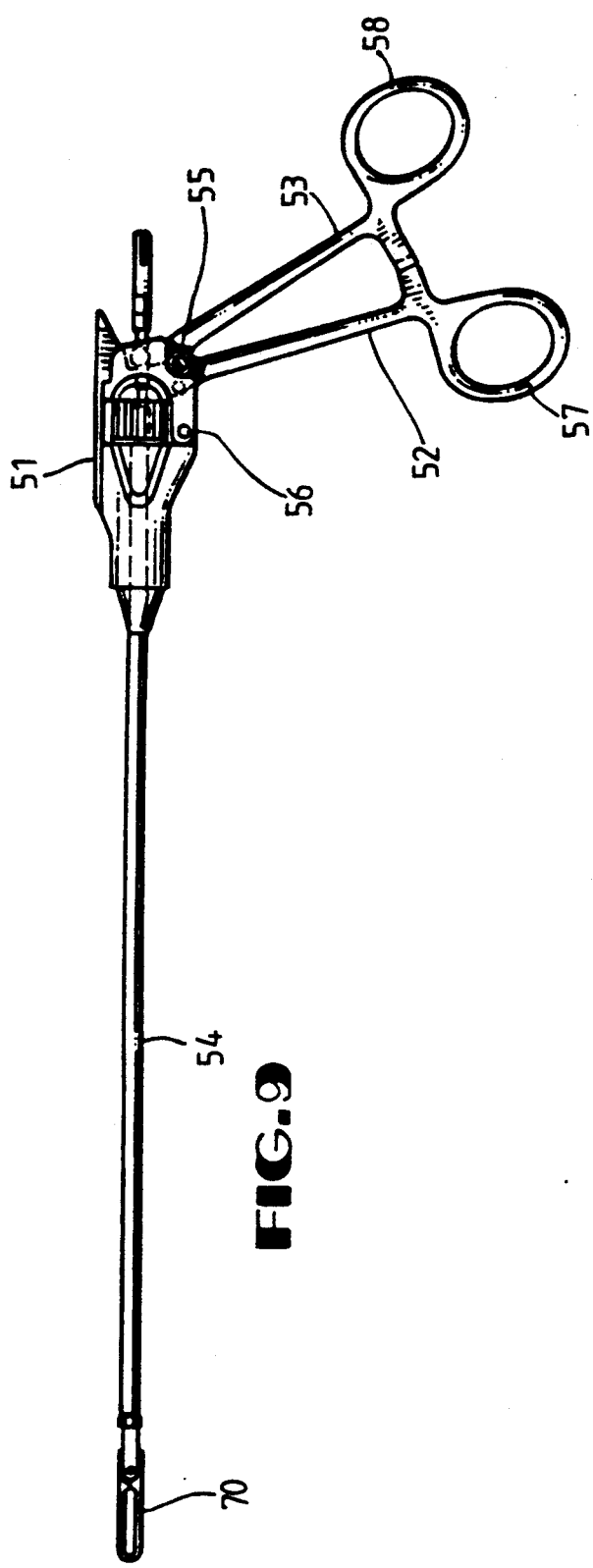
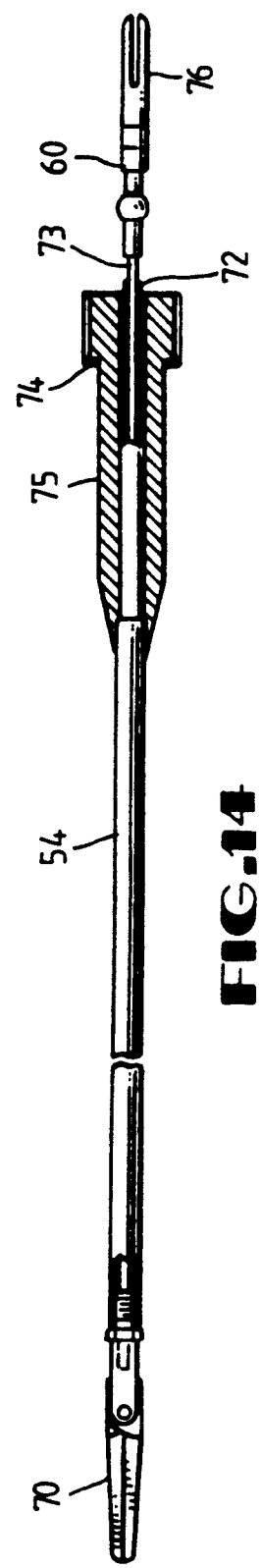

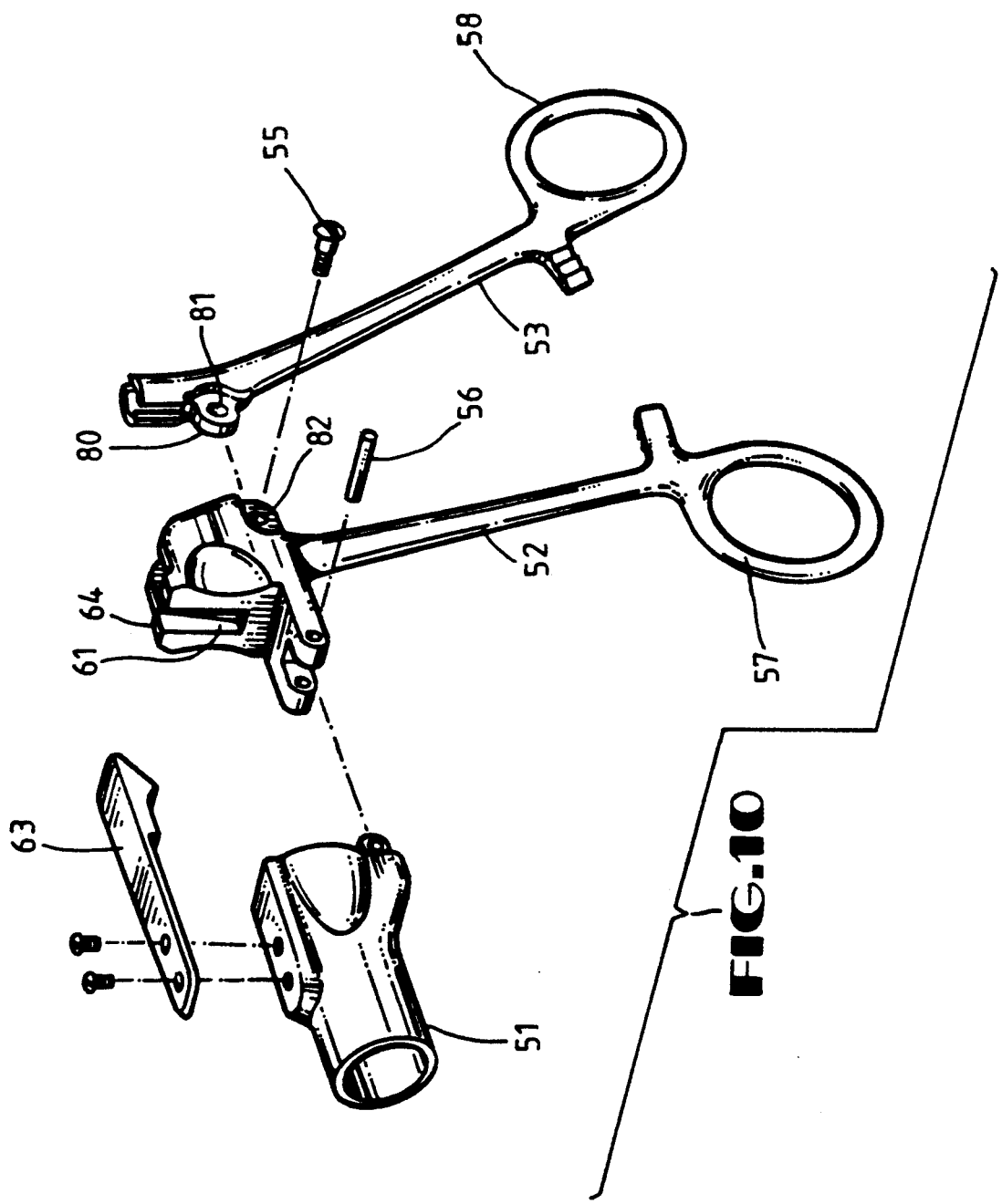

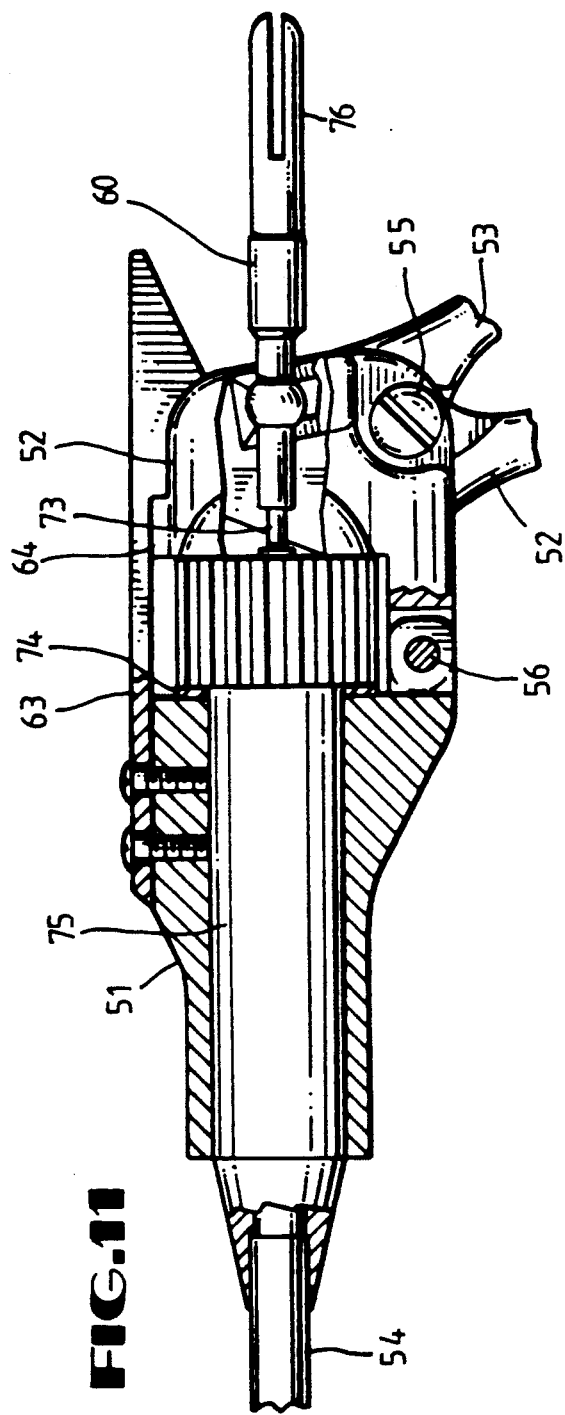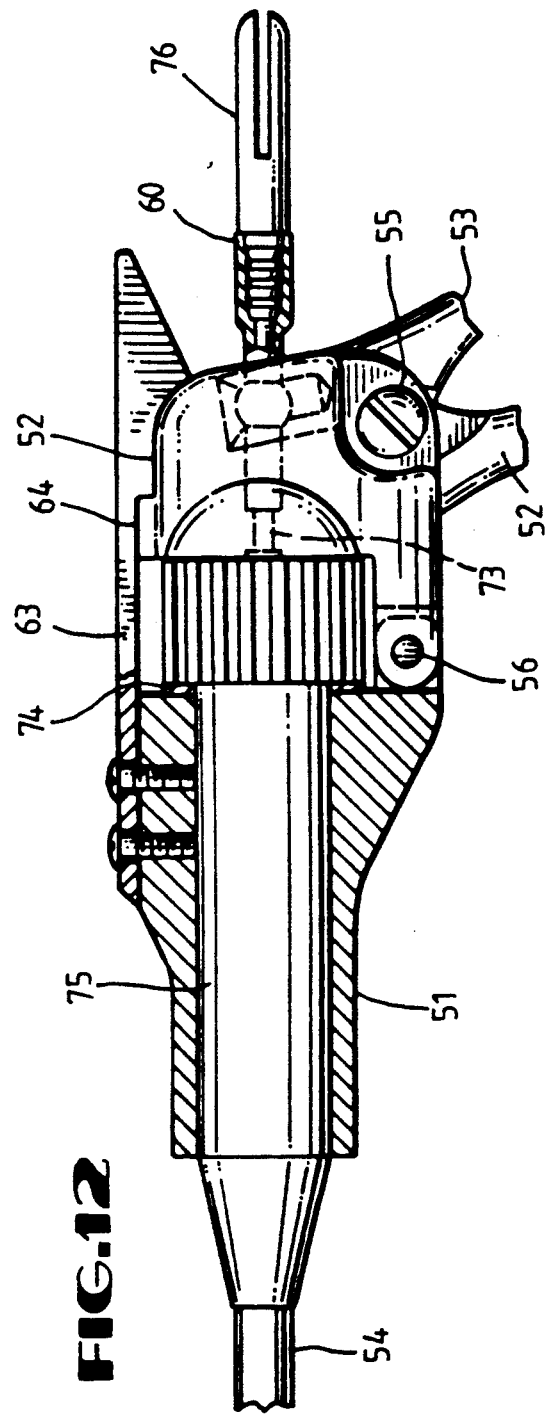

SURGICAL INSTRUMENT

BACKGROUND OF THE INVENTION

1. Field of the Invention

The present invention pertains to surgical instruments and, more particularly, to instruments for endoscopic surgery containing a disposable working member and a reusable handle member.

2. Discussion of the Prior Art

Endoscopic surgery is generally characterized as a form of surgery which requires only small incisions or portals for insertion of diagnostic and surgical instruments manipulated externally of the body. It is performed on various parts of the body, including body joints. It is preferable over open surgery to reduce the trauma associated with large incisions as well as the hospitalization and prolonged recovery periods required with open surgery. It is typically used, whenever it is possible, to achieve the same results as open surgery without incurring the disadvantages thereof. Endoscopic techniques include internal viewing for diagnosis and identification of problems as well as surgical operations such as meniscus removal or repair, cholecystectomy, appendectomy, vagotomy, lymphadenectomy, adhesiolysis, thoracic, bowel resection and hernia repair.

Traditional open surgical instruments are manufactured to a high standard of quality from stainless steel. After each use, the instruments are resterilized for the next operation. Endoscopic surgery requires instruments that can be partially inserted through small portals or incisions. As a result, at least the body-entering portion of endoscopic instruments tend to be small diameter stem assemblies constructed of long extended tubes. Unfortunately, the small diameter parts which enter the body cavity are difficult to clean and sterilize, and are also the most delicate and susceptible to wear. During an operation, blood and body fluids tend to accumulate inside the tubes of the stem assemblies. The risk of cross contamination exists if blood and body fluids are not removed from the instruments.

Disposable endoscopic instruments were introduced to eliminate the risk of cross contamination. Since the instruments are discarded after use, there has been no need to remove the blood and body fluids that accumulate in the instruments. However, the use of completely disposable endoscopic instruments has also proved to be very costly. In addition, the quality and operability of disposable instrument have proven to be less than what surgeons had grown accustomed to with traditional open instruments. The surgical instruments of the present invention address the problems associated with the prior art instruments by providing an endoscopic instrument which reduces the risk of cross contamination in the same way as a disposable instrument, but which also provides greater quality and operability at a lower cost. This is done by combining a disposable working member with a reusable handle member. The combination of a disposable working member and a reusable handle member also allows the use of a variety of types and sizes of working members with the same handle member.

SUMMARY OF THE INVENTION

The present invention relates in a broad aspect to a surgical instrument which comprises a disposable working member and a reusable handle member. Although the surgical instruments of the present invention is particularly suited for endoscopic surgery, the instrument can be readily used in open surgery as well. The disposable member, or stem assembly, typically includes such parts as a shaft, tubing, an actuator rod, and jaws or other working tips. These are the parts which enter the body cavity and are the most difficult to clean and sterilize, as well as being the most delicate and susceptible to wear. The disposable member typically also includes an adapter, and may also include an insulator and an electrocautery post when electrocauterization of tissue is desired. The reusable member is the handle or stock assembly held by a surgeon. As a permanent instrument, the handle assembly may be manufactured to a high standard of quality, thereby providing superior control and performance for the surgeon.

The invention includes a handle that is especially designed for quick and easy loading of a new disposable working member. In a preferred form the handle comprises a hinged barrel adapted to receive the working member, and a linkage for manipulating the working member. The handle preferably is built to accommodate disposable members in a variety of types, shapes and sizes, and to require no screws to lock the disposable member in position. Instead, the barrel of the handle member is closed by simply flipping or snapping a latch in place. An actuator rod engages the linkage when the barrel is closed. The handle member of the present invention requires only a small number of parts which are preferably made of durable stainless steel or other biocompatible materials.

BRIEF DESCRIPTION OF THE DRAWINGS

FIG. 2 is an exploded view of the handle member for an endoscopic surgical instrument of the present invention.

FIGS. 4, 5 and 6 are enlarged views of a yoke and rod embodiment of the present invention.

FIG. 7 is a side view of the stem assembly for the yoke and rod embodiment of the present invention.

FIGS. 8a, 8b, 8c and 8d illustrate how a stem assembly is removed from the handle member of the present invention.

FIG. 9 is a side view of another embodiment of an endoscopic surgical instrument of the present invention.

FIG. 10 is an exploded view of the handle member of FIG. 9.

FIGS. 11, 12 and 13 are enlarged views of a ball and socket embodiment of the present invention.

FIG. 14 is a side view of the stem assembly for the ball and socket embodiment of the present invention.

DESCRIPTION OF A PREFERRED EMBODIMENT

Figure 1:
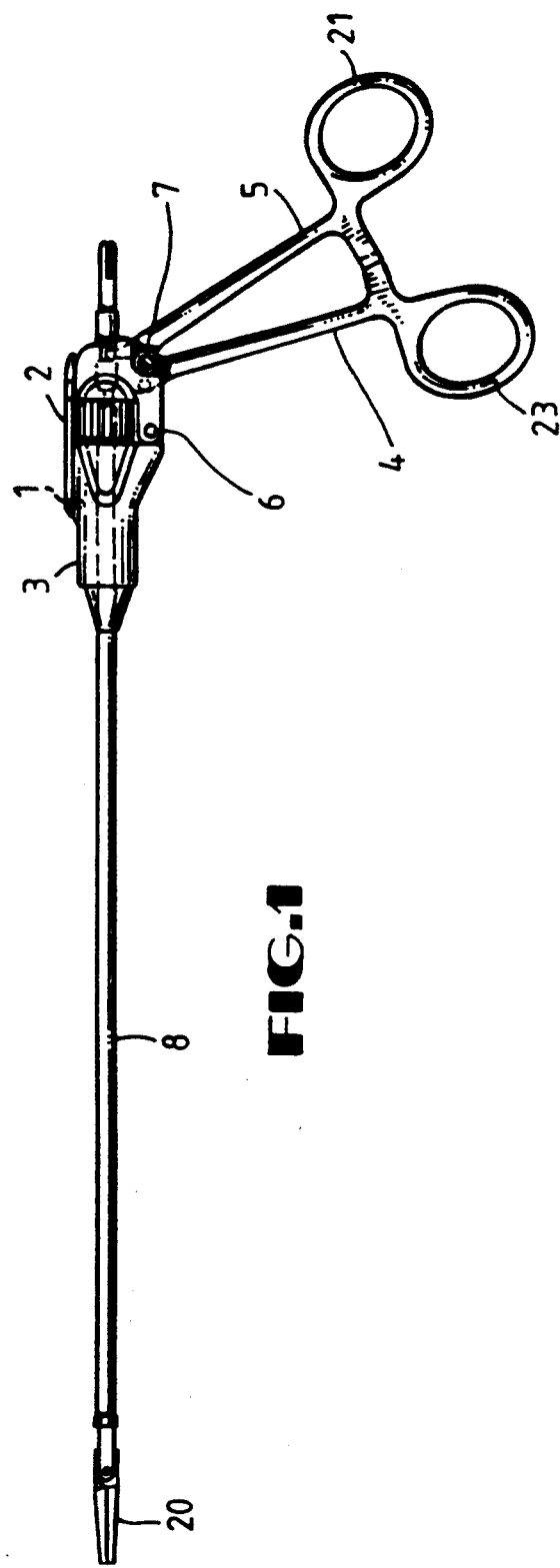
FIG. 1 is a side view of an endoscopic surgical instrument of the present invention.

A preferred endoscopic surgical instrument according to the present invention is shown in FIGS. 1–8. The embodiment illustrated in FIGS. 1–8 utilizes a yoke and rod linkage for activating jaws 20. The reusable handle member, as illustrated in FIG. 2, comprises a stationary front arm 4, moveable back arm 5, hinged barrel 3 and latch 2. Front arm 4 has a finger ring 23 at its lower end and a recess or passageway 35 at its upper end. The U-shaped recess 35 enables the rear portion of a stem assembly 8 to pass through the top of front arm 4 when barrel 3 is rotated to its closed position. Front arm 4 has an extension on top of one side of recess 35 in which groove 31 is machined.

Moveable back arm 5 is pivotally attached to the rear of front arm 4 by means of shouldered screw 7, allowing the back arm 5 to move freely about the pivot. A tongue portion 13 of the back arm 5 fits within a recess (not shown) at the back of the front arm 4 with matching pivot holes 14 and 15. The screw 7 extends through the pivot holes 14 and 15. The back arm 5 has a finger ring 21 at one end and a yoke 22 at the other end. Yoke 22, in the shape of a pair of vertically oriented posts, engages connector 10 of the stem assembly. Finger rings 21 and 23 enable a surgeon to grip and operate the instrument.

Barrel 3 is hinged to the front of front arm 4 by means of the hinge pin 6, which passes through the hinge and is then peened into place, allowing barrel 3 to rotate about hinge pin 6. When barrel 3 is rotated to a substantially horizontal position, the bore of barrel 3 is axially aligned with recess 35. Front arm 4 serves, in effect, as a stock for engaging the breech or proximal end of the barrel 3. Latch 2 is attached to the flat top of barrel 3 by a shouldered screw 1, enabling latch 2 to rotate about a plane parallel to the flat top of barrel 3. Latch 2 has a catch 30 located on one side near the end opposite from shoulder screw 1. After barrel 3 is rotated from a substantially vertical position to a substantially horizontal position, latch 2 (as depicted in FIG. 2) is rotated counterclockwise about shouldered screw 1 until catch 30 engages groove 31, thereby securing the barrel to the top of front arm 4. Catch 30 is disengaged from groove 31 by rotating latch 2 in a clockwise direction.

Figure 3:
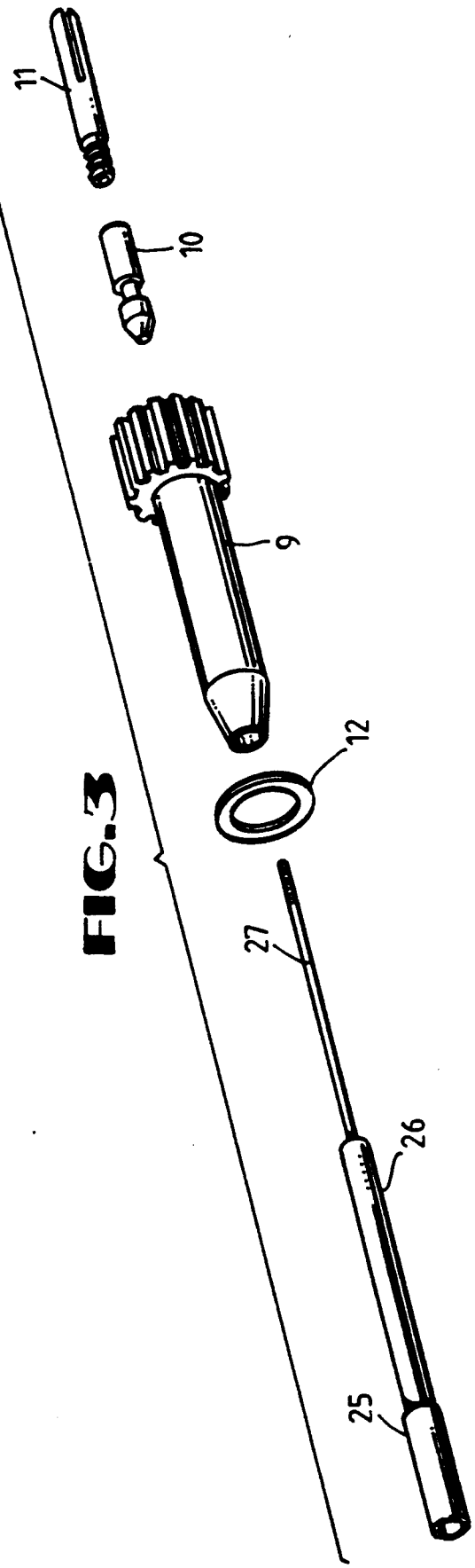
FIG. 3 is an exploded view of the proximal portion of a disposable stem assembly of the present invention.
Figure 8D:
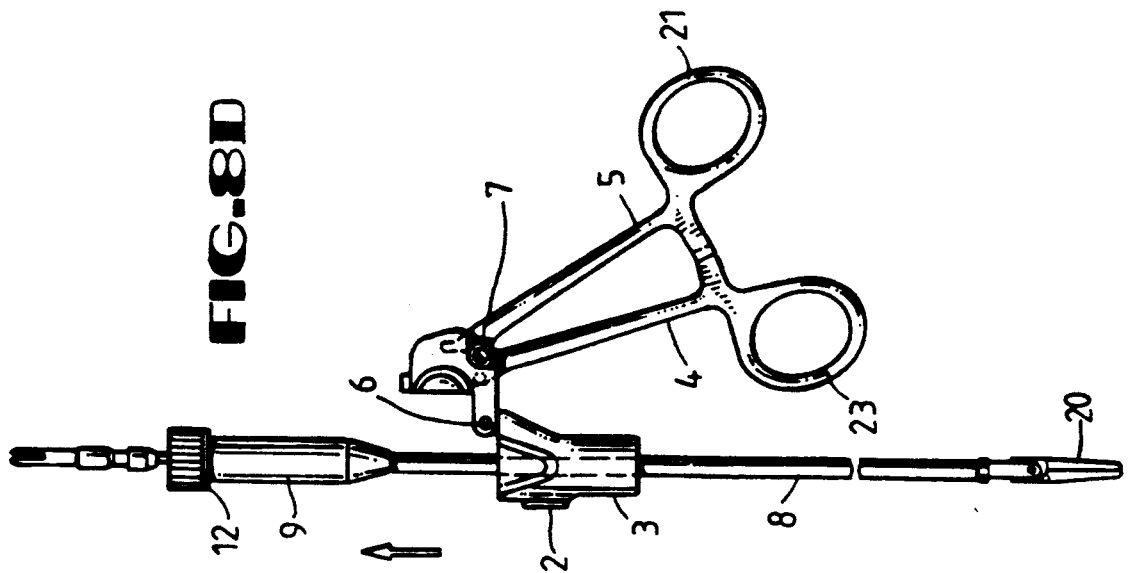
Figure 8C:
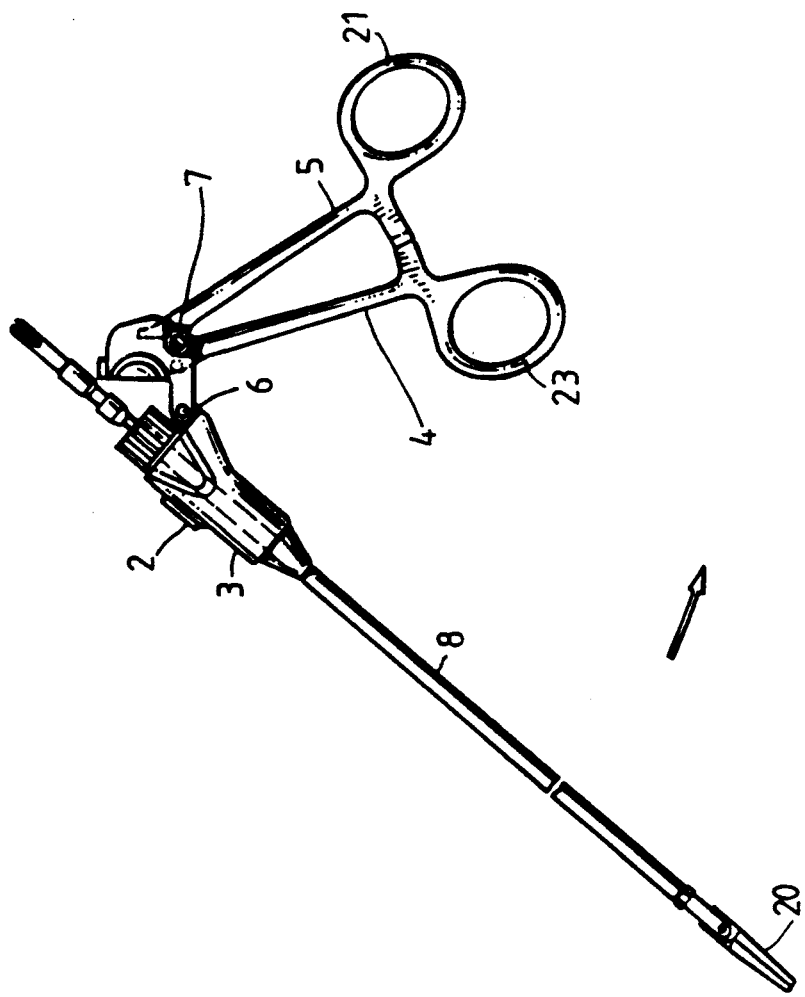

Stem assembly 8 of the yoke and rod embodiment of the present invention is shown in FIGS. 3 and 7. Stem assembly 8 comprises jaws 20 at the distal end, shaft 25, tubing 26, actuator rod 27, washer 12, adapter 9, connector 10, and electrocautery post 11. Tubing 26 and washer 12 are preferably made of teflon or other suitable synthetic material. Tubing 26 facilitates the movement of actuator rod 27 within the stem assembly. Shaft 25 is preferably made of stainless steel. Shaft 25 is insulated for electrocautery, preferably with kynar shrink wrap. The washer 12 is a friction fit over the front of the adapter 9 and is pressed into place against the shoulder of the larger radius at the end of the adapter 9. Adapter 9 is then slipped over the end of actuator rod 27, tubing 26 and shaft 25 of the stem assembly and may be fixed in place to the shaft with adhesive or ultrasonics staking. The end of actuator rod 27 is threaded and extends through adaptor 9. The connector 10 has a hole through its center with a larger bore at the back end. The larger bore is fitted over the step end of the electrocautery post 11 and held in place by a suitable means such as ultrasonic welding. The electrocautery post, which is also bored and tapped on the step end, with the connector 10 attached, is fitted over the actuator rod 27 of the stem assembly and screwed onto the threaded end of actuator rod 27. Alternatively, the electrocautery post 11 may be attached to the connector using an adhesive.

To assemble the instrument the latch 2 of the handle assembly must be disengaged, enabling the barrel 3 to rotate downward until the breech is clear. The disposable stem assembly is then inserted through the barrel 3 jaws first. The disposable stem assembly guides itself into position until the shoulder of the adapter 9 contacts the back of the barrel 3, with the washer 12 in between. Barrel 3, with the disposable stem assembly in place, is then rotated upward, compressing the washer 12 and the shoulder of the adapter 9 into the front arm 4. Adaptor 9 is preferably constructed from a thermoplastic such as noryl plastic. Washer 12 is preferably constructed from teflon and is readily compressible. Compressing the washer and adaptor between the barrel and front handle stabilizes the stem assembly within the handle member. The connector 10 and electrocautery post 11 pass through recess 35 in the front arm 4. The groove in the connector 10 engages yoke 22 of the back arm 5 to provide the drive for the actuator rod. When these are in place, the latch 2 may be rotated to engage the front arm 4 and lock the disposable element in place.

An electric current may be applied to the electrocautery post 11 when it is desired to cauterize tissue or vessels with jaws 20. Actuator rod 27 and jaws 20 are normally metal, thus allowing an electric current to travel from the electrical source through the electrocautery post and actuator rod to the jaws. The reusable handle member, preferably being metal, must be insulated from the electric current. The handle member may be coated with insulated material, or connector 10 may be constructed of an insulating material, such as noryl thermoplastic. Connector 10 as depicted in FIGS. 1-8 is an insulator. When electrocauterization capability is not desired, electrocautery post 11 may be omitted from the stem assembly. With such an embodiment, actuator rod 27 is secured to connector 10.

FIGS. 8a, 8b, 8c and 8d illustrate how the disposable stem assembly is removed from the reusable handle. To release the barrel, latch 2 is rotated away from the front arm. The barrel and stem assembly are rotated downward to clear the breech. The stem assembly is removed by lifting the assembly in an upward direction as indicated by the arrow in FIG. 8d. The reverse procedure is used to load a new stem assembly into the reusable handle. The instrument is preferably designed for quick and easy loading and unloading of stem assemblies having a variety of jaws or other working tips.

When the stem assembly is locked into the reusable handle, jaws 20 may be activated by the surgeon by manipulating the moveable back arm 5 with respect to front arm or stock 4. Moving back arm 5 moves actuator rod 27 axially within the stem assembly via yoke 22 and connector 10. The jaws are opened by pivoting moveable arm 5 away from stationary arm 4 using the finger and thumb, respectively. The jaws are closed by the reverse action. The operation of the jaws of the endoscopic surgical instrument and the actuator rod is well-known in the medical field. The surgical instrument of the present invention may be used with a variety of conventional jaw or forcep assemblies such as allis jaws, crile jaws, mixter jaws, scissors and needle holders. The jaw assemblies may be interchangeable.

Another embodiment of the present invention is illustrated in FIGS. 9-14. This embodiment utilizes a ball and socket linkage for actuating jaws 70. Referring to FIG. 10, the reusable handle member comprises barrel 51, front arm 52, back arm 53, hinge pin 56 and handle pivot screw 55. The front and rear arms have finger rings 57 and 58, respectively, which enable a surgeon to grip and operate the instrument. At the top of front arm 52 is a U-shaped recess or passageway 61 which enables the rear or proximal portion of stem assembly 54 to pass through when barrel 51 is rotated to its closed position. The bore of barrel 51 is axially aligned with the U- shaped recess 61 when the barrel is in its closed, or generally horizontal, position.

Back arm 53 is pivotally attached to the upper rear portion of front arm 52 through holes in the pivot by means of shouldered screw 55, enabling the back arm 53 to move freely about the pivot. A tongue portion 80 of the back arm 53 fits within a recess (not shown) at the back of the front arm 52 with matching pivot holes 81 and 82. The screw 55 extends through the pivot holes 81 and 82. The uppermost tip of back arm 53 has a pair of vertically oriented posts for engaging connector 60 of the stem assembly.

Barrel 51 is hinged to the upper front portion of front arm 52 as shown in FIGS. 10–12, by means of hinge pin 56. Hinge pin 56 passes through the hinge and is peened into place allowing barrel 51 to rotate about the hinge pin. The top of barrel 51 includes a thin, flexible extension 63 which extends backwards toward the front arm. Extension 63 functions as a latching mechanism for latching barrel 51 to the top of front arm 52 after the barrel has been rotated upwardly to a substantially horizontal or closed position. Extension 63 includes a shoulder which fits behind dual posts 64 on the top of front arm 52 which locks the barrel to the front arm. To unlatch the barrel, upward pressure is applied to the end of extension 63. Extension 63 may be an integral part of barrel 51 as shown in FIGS. 11 and 12 or may be secured to barrel 51 by screws, or other equivalent means, as shown in FIG. 10.

Figure 13:
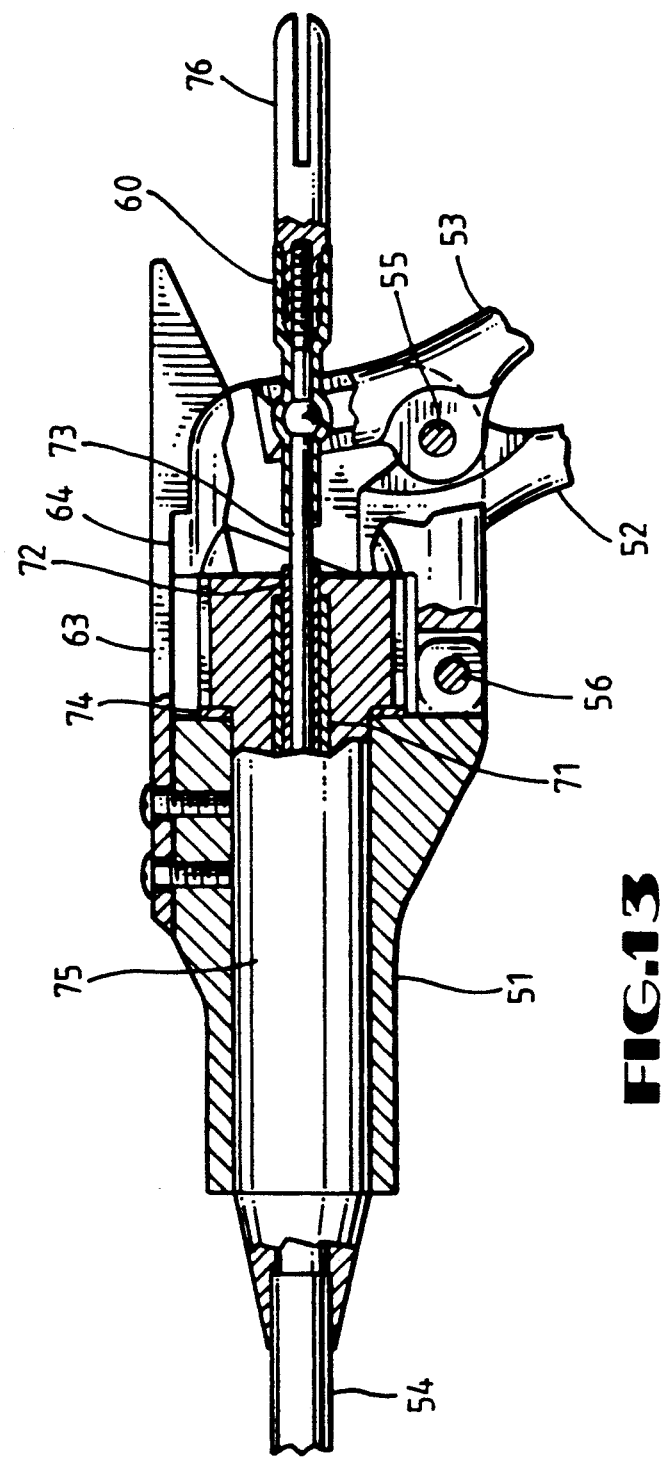

Stem assembly 54, as illustrated in FIGS. 9, 13 and 14, comprises jaws 70 at the distal end, a protective shaft 71, tubing 72, actuator rod 73, washer 74, adapter 75, connector 60 and electrocautery post 76. Stem assembly 54 is similar to the stem assembly described above in the yoke and rod embodiment of the present invention. Unlike the previous stem assembly however, a portion of connector 60 is shaped like a ball. A pair of indentations or sockets, which correspond to the ball shape portion of connector 60, are located inside the vertically oriented posts on top of back arm 53. Connector 60 will engage the indentations or sockets when barrel 51 rotates the stem assembly into the reusable handle.

To assemble the instrument, extension 63 of the barrel must be disengaged, enabling the barrel 51 to rotate downward until the breach has cleared. The disposable stem assembly is then inserted through the open barrel jaws first. The disposable stem assembly guides itself into position until the shoulder of the adapter 75 contacts the back of the barrel 51, with the washer 74 in between. The barrel 51, with the disposable stem assembly in place, is then rotated upward, compressing the washer 74 and the shoulder of the adapter 75 into the front arm 52. Connector 60 and electrocautery post 76 pass through the slot in the front arm 52. The ball shaped portion of connector 60 engages the sockets of the vertically oriented posts of back arm 53 to provide the drive for actuator rod 73. Simultaneously, extension 63 snaps behind post 64 on the top of front arm 52 and locks the disposable stem assembly into the reusable handle assembly.

Connector 60 may be constructed of an insulating material, such as noryl thermoplastic. When electrocauterization capability is not desired, electrocautery post 76 may be omitted from the stem assembly. With such an arrangement actuator rod 73 is secured to connector 60.

Although the electrocautery post has been depicted as being axially aligned with the stem assembly and the above described embodiments, it should be understood that the electrocautery post may be positioned in a variety of locations. By way of example, the electrocautery post may be positioned immediately behind the adapter, extending upward at a 90° angle to the stem assembly. In another embodiment, the electrocautery post may be positioned on the front arm behind the hinge for the barrel and extending downward at a 45° angle from the stem assembly.

It should also be noted that the latching mechanism for locking the barrel to the handle member in the ball and socket embodiment could also be used in the yoke and rod embodiment and vice versa. In addition, the latching mechanisms described above are meant to be illustrative only and not be taken in a limiting sense.

While the preferred embodiments utilize jaws or forceps, the surgical instrument of the present invention is usable with other working tips. All that is required is that two components actuated by the handle assembly move relative to each other at the distal tip of the instrument.

The disposable stem assembly may be manufactured in a variety of diameter sizes in order to accommodate use of the instrument through different size cannulas. The barrel portion of the handle may also be manufactured in a variety of shapes and sizes to accommodate different working members. By way of example, the barrel may be in a split ring shape instead of the continuous cylindrical shape depicted in the accompanying figures. Another embodiment may have a tube that is an integral part of the barrel extending from the handle towards the distal tip of the instrument. The extension tube would serve the same function as the shaft portion of the stem assembly as shown in FIGS. 3 and 4, but would be part of the reusable handle member. With such an embodiment, the disposable stem assembly may be configured without shaft 25.

In yet another embodiment, the disposable stem assembly may include a knurled knob near its proximal end for rotating the stem assembly relative to the reusable handle. This means for rotating the stem assembly enhances the operability of the instrument by allowing a surgeon to vary the orientation of the working tip relative to the handle. By way of example, the larger radius end of adapter 9, as shown in FIG. 3, is a knurled knob usable for rotating the stem assembly relative to the handle assembly.

It will be understood by those skilled in the art that certain variations and modifications may be made without departing from the spirit and scope of the invention as defined herein and in the appended claims.

What is claimed is:

1. Medical apparatus comprising:
    (a) a reusable handle assembly, including:
        (1) a stock having a proximal end and a distal end relative to a user of the apparatus and a longitudinal passageway, the stock configured to be manually held; and
        (2) a barrel having a proximal and distal end relative to a user of the apparatus, the barrel hinged at its proximal end to the stock and movable to a closed position that positions the proximal end of the barrel in abutting relation with the distal end of the stock; and
    (b) a disposable stem assembly having a proximal end and a distal end relative to a user of said apparatus, the stem assembly having a working tip at its distal end and configured at its proximal end to enter within the barrel and the passageway; and (c) a manually operable linkage linking the handle assembly and the stem assembly such that manual operation of the linkage activates the working tip of the stem assembly.

2. Medical apparatus comprising:

(a) a reusable handle assembly, including:

(1) a front handle member having an upper and a lower end, a stock at the upper end of the front handle member, and adapted to be held by a surgeon at the lower end of the front handle member, the stock having a proximal end and a distal end relative to a user of the apparatus, and a longitudinal passageway;

(2) a back handle member pivotally connected at one end to the proximal end of the stock of the front handle member and adapted to be held by a surgeon at the other end; and (3) a barrel having a proximal and distal end relative to a user of the apparatus, the barrel hinged at its proximal end to the stock and moveable to a closed position that positions the proximal end of the barrel in abutting relation with the distal end of the stock of the front handle member; and (b) a disposable stem assembly having a proximal end and a distal end relative to a user of the apparatus, the stem assembly having a working tip at its distal end and configured at its proximal end to enter within the barrel and the passageway; and (c) a manually operable linkage linking the handle assembly and the stem assembly such that manual operation of the linkage activates the working tip of the stem assembly.

3. Medical apparatus comprising:

(a) a disposable stem assembly having a proximal end and a distal end relative to a user of said apparatus, the disposable stem assembly having a working tip at its distal end;

(b) a reusable handle assembly, including:

(1) a stock having a longitudinal passageway, the stock configured to be manually held; and (2) a receptable hinged to the stock so that the receptacle pivots within a plane aligned with the axis of the disposable stem assembly, the receptacle being moveable to a closed position to secure and axially align the proximal end of the disposable stem assembly within the longitudinal passageway; and (c) a manually operable linkage linking the handle assembly and the stem assembly such that manual operation of the linkage activates the working tip of the stem assembly.

4. The apparatus of claim 1, 2 or 3, wherein the linkage comprises a ball and socket joint wherein the ball is mounted on either the stem assembly or the handle assembly, and the socket is mounted on the other assembly.

5. The apparatus of claim 1, 2 or 3 wherein the linkage includes a yoke adapted to interconnect the stem assembly and the handle assembly.

6. The apparatus of claim 1 or 2 further comprises a latch operable to lock the barrel to the stock when in abutting relation.

7. The apparatus of claim 3 further comprises a latch operable to lock the receptacle in a closed position to the stock.

8. The apparatus of claim 1, 2 or 3 wherein the working tip comprises moveable jaws.

9. The apparatus of claim 1, 2 or 3 further comprises a knob on the proximal end of the disposable stem assembly for rotating the stem assembly relative to the handle assembly.

10. The apparatus of claim 1, 2 or 3 further comprises an electrocautery post for providing an electrical current to the working tip.

* * * * *